(12) United States Patent
Hamer

(10) Patent No.: US 9,211,312 B2
(45) Date of Patent: Dec. 15, 2015

(54) METHOD OF TREATING PERIPHERAL NERVE DISORDERS

(75) Inventor: John Hamer, London (GB)

(73) Assignee: Volution Immuno Pharmaceuticals SA, Geneva (CH)

(*) Notice: Subject to any disclaimer, the term of this patent is extended or adjusted under 35 U.S.C. 154(b) by 1610 days.

(21) Appl. No.: 12/440,462

(22) PCT Filed: Sep. 10, 2007

(86) PCT No.: PCT/GB2007/003401
§ 371 (c)(1),
(2), (4) Date: Dec. 31, 2009

(87) PCT Pub. No.: WO2008/029167
PCT Pub. Date: Mar. 13, 2008

(65) Prior Publication Data
US 2010/0111929 A1 May 6, 2010

(30) Foreign Application Priority Data
Sep. 8, 2006 (GB) .................................. 0617734.9

(51) Int. Cl.
*A61K 38/00* (2006.01)
*A61K 39/395* (2006.01)
*A61K 35/30* (2015.01)
*A61K 38/17* (2006.01)

(52) U.S. Cl.
CPC ..................................... *A61K 38/17* (2013.01)

(58) Field of Classification Search
None
See application file for complete search history.

(56) References Cited

U.S. PATENT DOCUMENTS

2006/0115476 A1 6/2006 Tedesco et al.
2008/0220003 A1* 9/2008 Schnatbaum et al. ..... 424/178.1

FOREIGN PATENT DOCUMENTS

| WO | 03062278 | 7/2003 |
| WO | WO 2004/007553 | * 1/2004 |
| WO | 2004106369 | 12/2004 |
| WO | 2005023866 | 3/2005 |
| WO | 2008030505 | 3/2008 |

OTHER PUBLICATIONS

Hartung et al (Neurology 37: 1006-9, 1987—abstract only).*
Scheithauer et al (Brit J Cancer 77: 1349-1354, 1998).*
Winer (QJ Med 95: 717-721, 2002).*
Halstead et al., "C5 inhibitor rEV576 protects against neural injury in an in vitro mouse model of Miller Fisher syndrome", Journal of the Peripheral Nervous System, 2008, vol. 13, pp. 228-235.
Hartung et al., "Guillain-Barre syndrome: Activated complement components C3a and C5a in CSF", Neurology, 1987, vol. 37, pp. 1006-1009.
Hughes et al., "Guillain-Barre syndrome", Lancet, 2005, vol. 366, pp. 1653-1666.
Kieseier et al., "Advances in understanding and treatment of immune-mediated disorders of the peripheral nervous system", Muscle Nerve, 2004, vol. 30, pp. 131-156.
Mizuno et al., "Novel C5a regulators in inflammatory disease", Expert Opin Investig Drugs, 2005, vol. 14, pp. 807-821.
Nunn et al., "Complement inhibitor of C5 activation from the soft tick Ornithodoros moubata", Journal of Immunology, 2005, vol. 174, No. 4, pp. 2084-2091.
Zhang et al., "Early complement activation and decreased levels of glycosylphosphatidylinositol-anchored complement inhibitors in human and experimental diabetic retinopathy", Diabetes, 2002, vol. 51, pp. 3499-3504.
Sahu et al., "Complement inhibitors: A resurgent concept in anti-inflammatory therapeutics", Immunopharmacology, 2000, vol. 49, No. 1-2, pp. 133-148.
Morgan et al., "Blockade of the C5a receptor fails to protect against experimental autoimmune encephalomyelitis in rats", Clin Exp Immunol, 2004, 138, 430-438.
Roversi et al., "The structure of OMCI, a novel lipocalin inhibitor of the complement system", J Mol Biol, 2007, 369, 784-793.
Younger et al., "Complement activation in emergency department patients with severe sepsis", Academic Emergency Medicine, 2010, 17, 353-359.
Stoll et al., "Presence of the terminal complement complex (C5b-9) precedes myelin degradation in immune-mediated demyelination of the rat peripheral nervous system", Ann Neurol, 1991, 30:147-155.

* cited by examiner

*Primary Examiner* — Daniel E Kolker
*Assistant Examiner* — Aditi Dutt
(74) *Attorney, Agent, or Firm* — Fangli Chen; Suzanne Nguyen

(57) ABSTRACT

The invention relates to the use of agents that bind the complement protein C5 in the treatment of diseases associated with inappropriate complement activation, and in particular in the treatment of peripheral nerve disorders.

13 Claims, 11 Drawing Sheets

FIG. 2

```
ATGCTGGTTTTGGTGACCCTGATTTCTCCTTTTCTGCGAACATGCATATGCTGACAGC    60
 M  L  V  L  V  T  L  I  F  S  F  S  A  N  I  A  Y  A  D  S    20

GAAAGCGACTGCACTGGAAGCTGGAACCTGTGTTCCAAGCTTTCAGTGAGGGCAAA      120
 E  S  D  C  T  G  S  E  P  V  D  A  F  Q  A  F  S  E  G  K    40

GAGGCATATGTCCTGGTTCGTTCTGACCCAAAGCGAGGACTGCTTGAAAGGAGAA       180
 E  A  Y  V  L  V  R  S  T  D  P  K  A  R  D  C  L  K  G  E    60

CCAGCCGGAGAAAAGCAGGACAACACGTTGCCGGTGATGATGACGTTTAAGAATGGCACA  240
 P  A  G  E  K  Q  D  N  T  L  P  V  M  M  T  F  K  N  G  T    80

GACTGGGCTTCAACCGATTGGACGTTTACTTTGGACGGCGCAAAGGTAACGGCAACCCTT  300
 D  W  A  S  T  D  W  T  F  T  L  D  G  A  K  V  T  A  T  L   100

GGTAACCTAACCCAAAATAGGGAAGAAGTTCCAGATTATGAGATGTGGATGCTCGATGGCGAGGGCTT  360
 G  N  L  T  Q  N  R  E  V  V  Y  D  S  Q  S  H  H  C  H  V   120

GACAAGGTCGAGAAGGAAGTTCCAGATTATGAGATGTGGATGCTCGATGCTGGAGGGCTT  420
 D  K  V  E  K  E  V  P  D  Y  E  M  W  M  L  D  A  G  G  L   140

GAAGTGGAAGTCGAGTGCTGCCGTCAAAAGCTTGAAGAGTTGGCGTCTGGCAGGAACCAA  480
 E  V  E  V  E  C  C  R  Q  K  L  E  E  L  A  S  G  R  N  Q   160

ATGTATCCCCATCTCAAGGACTGCTAG                                   507
 M  Y  P  H  L  K  D  C  *                                    168
```

Anion exchange chromatography

Classical haemolytic assay of fractions

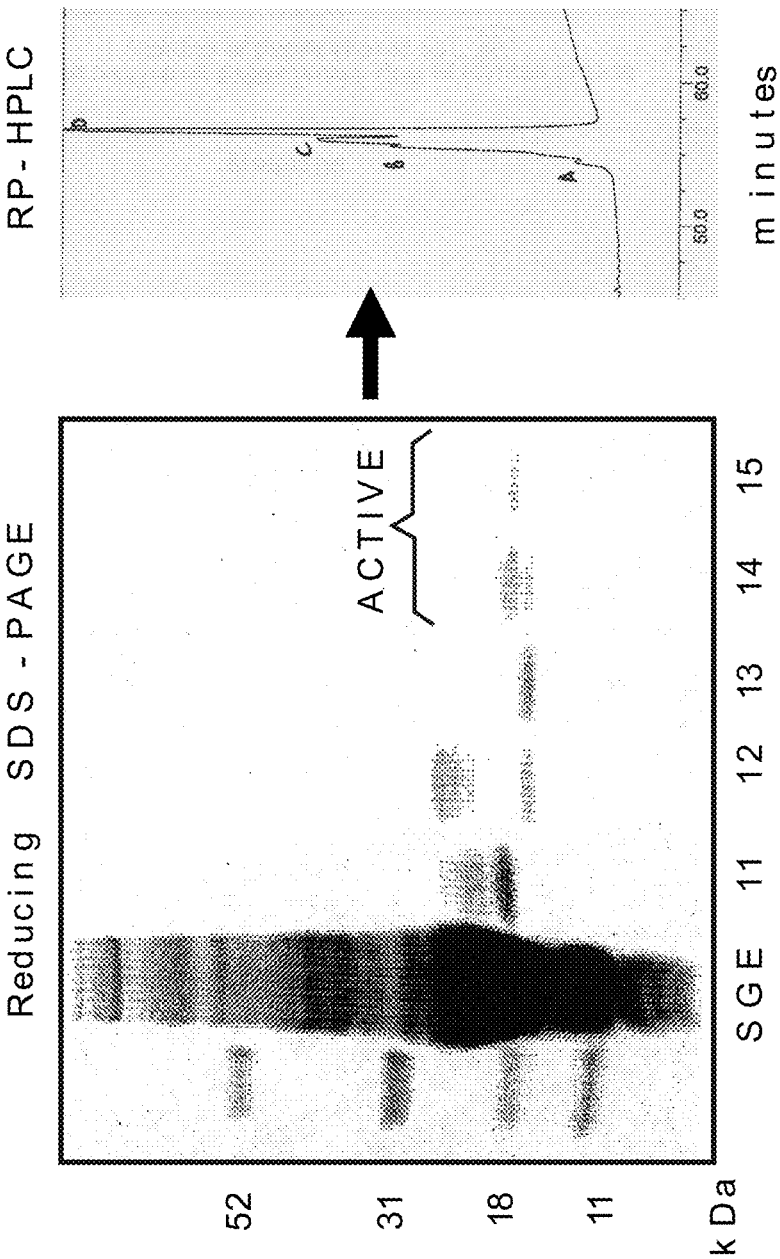

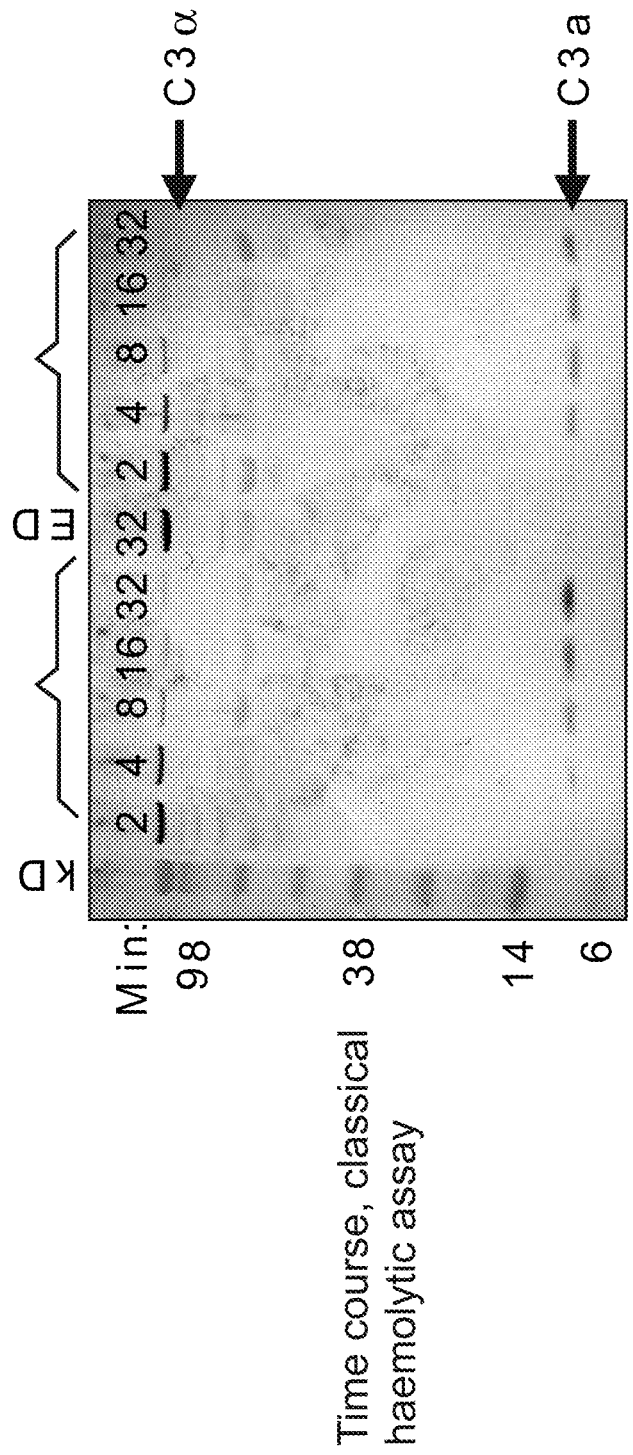

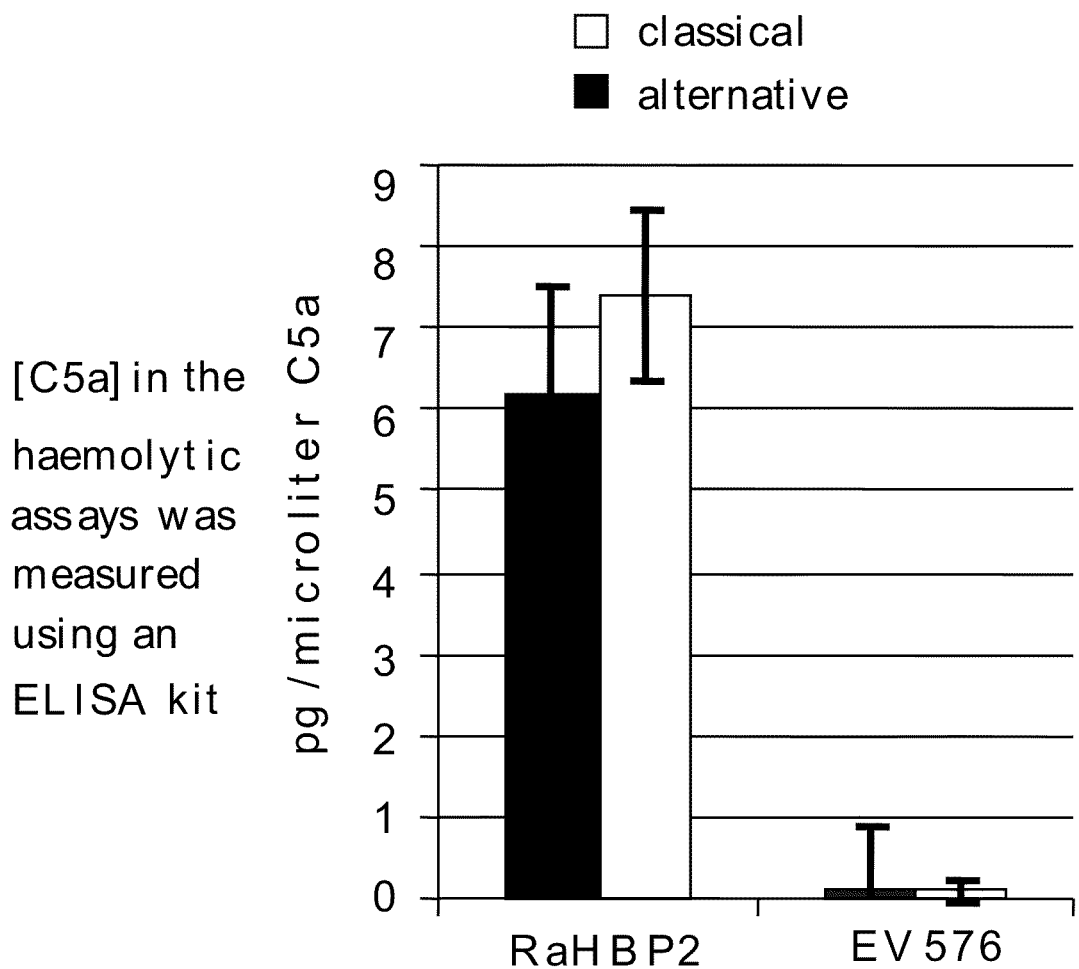

Binds directly to C5

EV576 and control (RaHBP2) were transferred to nitrocellulose and probed with radiolabelled C3 and C5

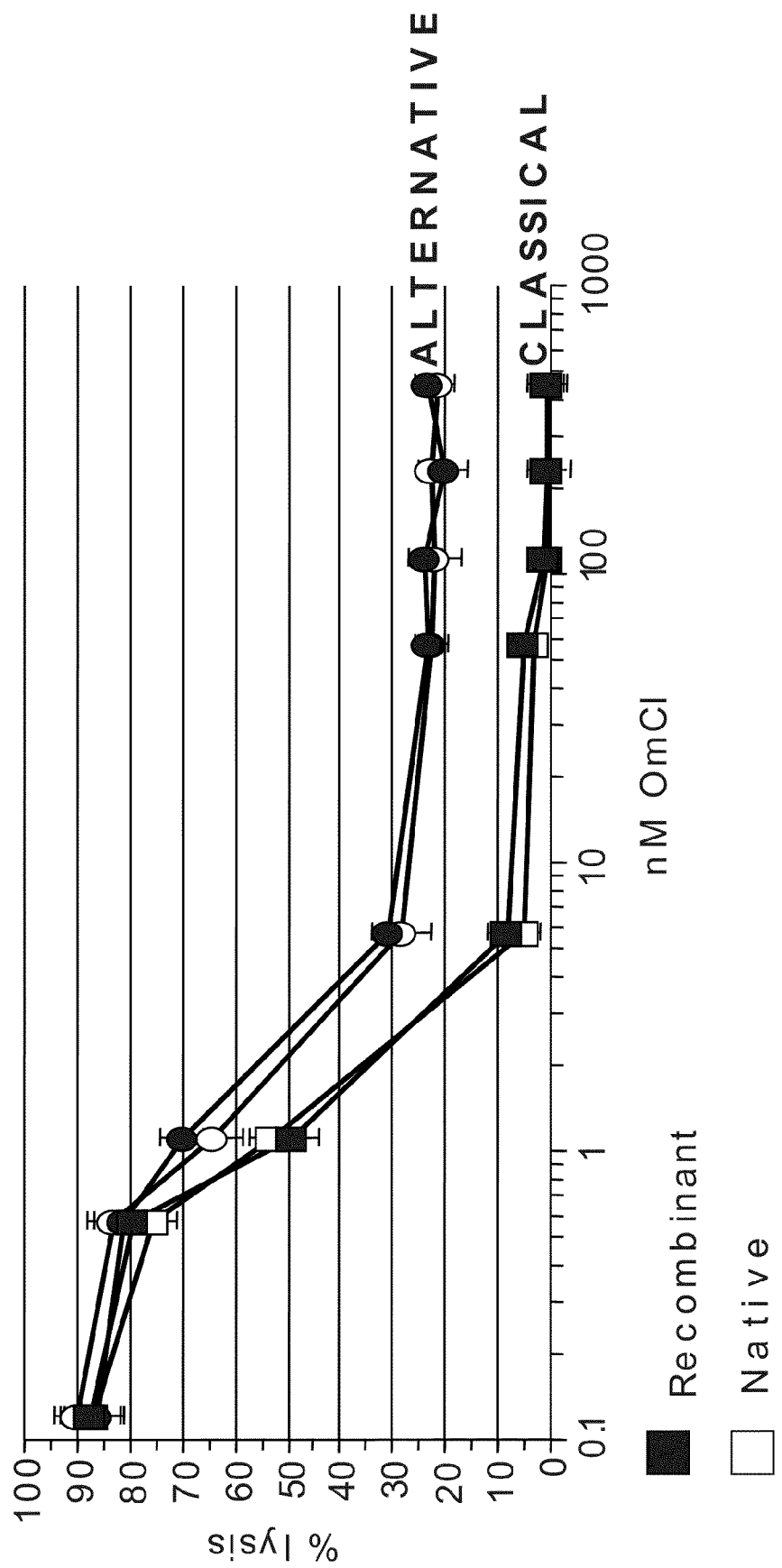

Structure

EV576 is an outlying member of the lipocalin family. It has 46% aa identity with moubatin, a platelet aggregation inhibitor from *O. moubata*.

FIG. 6A
WEIGHT LOSS

[Graph: Body weights (g) vs Days post immunization]

- ◇ no treatment
- □ high dose of rEV576
- △ low dose of rEV576
- ✕ PBS treatment

CLINICAL SCORES

— clinical scores no treatment
— clinical scores high dose of rEV576
— clinical scores low dose of rEV576
— clinical scores PBS treatment Treatment Severity of paresis was graded as follows:

0 = no illness;
1 = flaccid tail;
2 = moderate paraparesis;
3 = severe paraparesis;
4 = tetraparesis or death.

\* $P<0.01$ actives vs PBS
$P<0.001$ actives vs untreated

METHOD OF TREATING PERIPHERAL NERVE DISORDERS

CROSS REFERENCE TO RELATED APPLICATIONS

The present application is a National Stage Application claiming the priority of co-pending PCT Application No. PCT/GB2007/003401 filed Sep. 10, 2007, which in turn, claims priority from Great Britain application Serial No. 0617734.9 filed Sep. 8, 2006. Applicants claim the benefits of 35 U.S.C. §120 as to the PCT application and priority under 35 U.S.C. §119 as to the said Great Britain application, and the entire disclosures of both applications are incorporated herein by reference in their entireties.

The present invention relates to the use of agents that bind the complement protein C5 in the treatment of diseases associated with inappropriate complement activation, and in particular in the treatment of peripheral nerve disorders.

All documents mentioned in the text and listed at the end of this description are incorporated herein by reference.

BACKGROUND TO THE INVENTION

The complement system is an essential part of the body's natural defence mechanism against foreign invasion and is also involved in the inflammatory process. More than 30 proteins in serum and at the cell surface are involved in complement system function and regulation. Recently it has become apparent that, as well as the ~35 known components of the complement system which may be associated with both beneficial and pathological processes, the complement system itself interacts with at least 85 biological pathways with functions as diverse as angiogenesis, platelet activation, glucose metabolism and spermatogenesis [1].

The complement system is activated by the presence of foreign antigens. Three activation pathways exist: (1) the classical pathway which is activated by IgM and IgG complexes or by recognition of carbohydrates; (2) the alternative pathway which is activated by non-self surfaces (lacking specific regulatory molecules) and by bacterial endotoxins; and (3) the lectin pathway which is activated by binding of manna-binding lectin (MBL) to mannose residues on the surface of a pathogen. The three pathways comprise parallel cascades of events that result in the production of complement activation through the formation of similar C3 and C5 convertases on cell surfaces resulting in the release of acute mediators of inflammation (C3a and C5a) and formation of the membrane attack complex (MAC). The parallel cascades involved in the classical and alternative pathways are shown in FIG. 1.

Complement can be activated inappropriately under certain circumstances leading to undesirable local tissue destruction. Inappropriate complement activation has been shown to play a role in a wide variety of diseases and disorders including acute pancreatitis, Alzheimer's disease, allergic encephalomyelitis, allotransplatation, asthma, adult respiratory distress syndrome, burn injuries, Crohn's disease, glomerulonephritis, haemolytic anaemia, haemodialysis, hereditary angioedema, ischaemia reperfusion injuries, multiple system organ failure, multiple sclerosis, myasthenia gravis, ischemic stroke, myocardial infarction, psoriasis, rheumatoid arthritis, septic shock, systemic lupus erythematosus, stroke, vascular leak syndrome, transplantation rejection and inappropriate immune response in cardiopulmonary bypass operations. Inappropriate activation of the complement system has thus been a target for therapeutic intervention for many years and numerous complement inhibitors targeting different parts of the complement cascade are under development for therapeutic use.

In ischemic stroke and myocardial infarction, the body recognises the dead tissue in the brain or heart as foreign and activates complement so causing further local damage. Similarly in cardiopulmonary bypass operations, the body recognises the plastic surfaces in the machine as foreign, activates complement and can result in vascular damage. In autoimmune diseases, the body may wrongly recognise itself as foreign and activate complement with local tissue damage (e.g. joint destruction in rheumatoid arthritis and muscle weakness in myasthenia gravis).

In the peripheral nervous system, several types of neuropathy are autoimmune in origin and circulating autoantibodies to myelin and Schwann cell antigens have been detected [2]. Complement is implicated as an effector in inflammatory demyelination observed in experimental allergic neuritis (EAN), a model for Guillain-Barre syndrome, an immune-mediated acquired human demyelinating neuropathy [3].

Peripheral nerve disorders can be chronic and come on very slowly over several months or years. An example of such an illness is chronic inflammatory demyelinating polyradiculoneuropathy, known as CIDP. Sometimes peripheral nerve disorders are acute and come on very rapidly over the course of a few days, for example post-infective demyelinating polyradiculoneuropathy, better known as Guillain-Barre Syndrome (GBS). CIDP was once known as 'chronic GBS' and is regarded as a related condition to GBS.

GBS is a rare condition (prevalence is 1-2 per 100,000 or ~3,000 cases in the USA per year). About half the cases of GBS occur after a bacterial or viral infection. GBS is an autoimmune disorder in which the body produces antibodies that damage the myelin sheath that surrounds peripheral nerves. The myelin sheath is a fatty substance that surrounds axons, which increases the speed at which signals travel along the nerves.

Once these antibodies react with the antigen (the myelin sheath) the complement system is activated and C5 is produced. C5 breaks down to C5a and C5b which becomes C5b-9 (the membrane attack complex). C5a attracts white cells and C5b-9 opens blood vessels wall to allow white cell ingress into the tissues. Suitably stimulated white cells release destructive cytokines causing local damage to the nerves.

Clinically, GBS is characterised by weakness and numbness or tingling in the legs and arms, and possible loss of movement and feeling in the legs, arms, upper body, and face. The first symptoms of GBS are usually numbness or tingling (paresthesia) in the toes and fingers, with progressive weakness in the arms and legs over the next few days. Some patients experience paresthesia only in their toes and legs; others only experience symptoms on one side of the body.

The symptoms may stay in this phase, causing only mild difficulty in walking, requiring crutches or a walking stick. However, sometimes the illness progresses, leading to complete paralysis of the arms and legs. About one quarter of the time, the paralysis continues up the chest and freezes the breathing muscles, leaving the patient dependant on a ventilator. If the swallowing muscles are also affected, a feeding tube may be needed.

GBS is considered a medical emergency and most patients are admitted to intensive care soon after diagnosis. Though GBS can improve spontaneously, there are a number of treatments that facilitate recovery. Most patients with GBS and CIDP are treated with plasmapheresis (blood plasma exchange) or large doses of immunoglobulin. In extreme cases filtration of the CerebroSpinal Fluid has been used. Ventilation, plasmapheresis and immunoglobulin are extremely expensive.

There is thus a great need for agents that improve upon the currently available treatments for peripheral nerve disorders such as CIDP and GBS.

SUMMARY OF THE INVENTION

Accordingly, the invention provides a method of treating or preventing a peripheral nerve disorder comprising administering to a subject in need thereof a therapeutically or prophylactically effective amount of an agent that binds complement C5.

The invention also provides the use of a therapeutically or prophylactically effective amount of an agent that binds complement C5 in the manufacture of a medicament for treating or a preventing peripheral nerve disorder.

The peripheral nerve disorder of the present invention is selected from the group consisting of post-infective demyelinating polyradiculoneuropathy (Guillain Barré syndrome), Miller Fisher syndrome, acute inflammatory demyelinating polyradiculoneuropathy (AIDP), chronic inflammatory demyelinating polyradiculoneuropathy (CIDP), diabetic neuropathy, uraemic pruritus, multifocal motor neuropathy, paraproteinaemic neuropathy, anti-Hu neuropathy, postdiphtheria demyelinating neuropathy, multiple sclerosis, radiation myelopathy, giant cell arteritis (temporal arteritis), transverse myelitis, motor neurone disease, dermatomyositis.

Preferably, the peripheral nerve disorder is selected from the group consisting of Guillain Barr Syndrome, chronic inflammatory demyelinating polyradiculoneuropathy.

Preferably, the agent acts to prevent the cleavage of complement C5 by C5 convertase into complement C5a and complement C5b-9.

The complement C5 protein, also referred to herein as C5, is cleaved by the C5 convertase enzyme, itself formed from C3a, an earlier product of the alternative pathway (FIG. 1). The products of this cleavage include an anaphylatoxin C5a and a lytic complex C5b-9 also known as membrane attack complex (MAC). C5a is a highly reactive peptide implicated in many pathological inflammatory processes including neutrophil and eosinophil chemotaxis, neutrophil activation, increased capillary permeability and inhibition of neutrophil apoptosis [4].

MAC is associated with other important pathological processes including rheumatoid arthritis [5;6], proliferative glomerulonephritis [7], idiopathic membranous nephropathy [8], proteinurea [9], demyelination after acute axonal injury [10] and is also responsible for acute graft rejection following xenotransplantation [11].

C5a has become a target of particular interest in the field of complement-associated disorders [12]. Although C5a has many well-recognised pathological associations, the effects of its depletion in humans appear to be limited. Monoclonal antibodies and small molecules that bind and inhibit C5a or C5a receptors have been developed to treat various autoimmune diseases. These molecules do not, however, prevent the release of MAC.

In contrast, administration of an agent that binds C5 according to the first aspect of the invention, inhibits both the formation of C5a peptide and the MAC. Surprisingly, it has been found that inhibition of both C5a and the MAC reduces the clinical symptoms associated with peripheral nerve disorders. Furthermore, because C5 is a late product of the classical and alternative complement pathways, inhibition of C5 is less likely to be associated with risks of concomitant infection that exist when targeting earlier products in the cascade [13].

The ability of an agent to bind C5 may be determined by standard in vitro assays known in the art, for example by western blotting following incubation of the protein on the gel with labelled C5. Preferably, the agent according to the invention binds C5 with an $IC_{50}$ of less than 0.2 mg/ml, preferably less than 0.1 mg/ml, preferably less than 0.05 mg/ml, preferably less than 0.04 mg/ml, preferably less than 0.03 mg/ml, preferably 0.02 mg/ml, preferably less than 1 µg/ml, preferably less than 100 ng/ml, preferably less than 10 ng/ml, more preferably still, less than 1 ng/ml.

Preferably, the agent that binds C5 is derived from a haematophagous arthropod. The term "haematophagous arthropod" includes all arthropods that take a blood meal from a suitable host, such as insects, ticks, lice, fleas and mites. Preferably, the agent is derived from a tick, preferably from the tick Ornithodoros moubata.

According to one embodiment of the invention, the agent that binds C5 is a protein comprising amino acids 19 to 168 of the amino acid sequence in FIG. 2 or is a functional equivalent of this protein. The agent that binds C5 may be a protein consisting of amino acids 19 to 168 of the amino acid sequence in FIG. 2 or be a functional equivalent of this protein.

According to an alternative embodiment, the protein used according to this embodiment of the invention may comprise or consist of amino acids 1 to 168 of the amino acid sequence in FIG. 2, or be a functional equivalent thereof. The first 18 amino acids of the protein sequence given in FIG. 2 form a signal sequence which is not required for C5 binding activity and so this may optionally be dispensed with, for example, for efficiency of recombinant protein production.

The protein having the amino acid sequence given in FIG. 2, also referred to herein as the EV576 protein, was isolated from the salivary glands of the tick Ornithodoros moubata. EV576 is an outlying member of the lipocalin family and is the first lipocalin family member shown to inhibit complement activation. The EV576 protein inhibits the alternative, classical and lectin complement pathways by binding C5 and preventing its cleavage by C5 convertase into Complement C5a and Complement C5b-9, thus inhibiting both the action of C5a peptide and the MAC. The term "EV576 protein", as used herein, refers to the sequence given in FIG. 2 with or without the signal sequence.

The EV576 protein and the ability of this protein to inhibit complement activation has been disclosed in [19], where the EV576 protein was referred to as the "OmCI protein". It has now been found that the EV576 protein is surprisingly effective in the treatment and prevention of peripheral nerve disorders. The data presented herein demonstrate that EV576 reduces the degree of clinical disease even when given during the active disease phase in experimental autoimmune neuritis (EAN) in rats. EV576 thus represents a potential human therapy for the treatment and prevention of peripheral nerve disorders.

The surprising effectiveness of EV576 in the treatment of peripheral nerve disorders appears to be due to the fact that it acts by binding C5, thus inhibiting the formation of C5a and MAC.

According to a further embodiment of the invention, the agent may be a nucleic acid molecule encoding the EV576 protein or a functional equivalent thereof. For example, gene therapy may be employed to effect the endogenous production of the EV576 protein by the relevant cells in the subject, either in vivo or ex vivo. Another approach is the administration of "naked DNA" in which the therapeutic gene is directly injected into the bloodstream or into muscle tissue.

Preferably, such a nucleic acid molecule comprises or consists of bases 53 to 507 of the nucleotide sequence in FIG. 2. This nucleotide sequence encodes the EV576 protein in FIG. 2 without the signal sequence. The first 54 bases of the nucleotide sequence in FIG. 2 encode the signal sequence of which is not required for complement inhibitory activity. Alternatively, the nucleic acid molecule may comprise or consist of bases 1 to 507 of the nucleic acid sequence in FIG. 2, which encodes the protein with the signal sequence.

The EV576 protein has been demonstrated to bind to C5 and prevent its cleavage by C5 convertase in rat, mouse and human serum with an $IC_{50}$ of approximately 0.02 mg/ml. Preferably, functional equivalents of the EV576 protein which retain the ability to bind C5 with an $IC_{50}$ of less than 0.2 mg/ml, preferably less than 0.1 mg/ml, preferably less than 0.05 mg/ml, preferably less than 0.02 mg/ml, preferably less than 1 µg/ml, preferably less than 100 ng/ml, preferably less than 10 ng/ml, more preferably still, less than 1 ng/ml.

In one respect, the term "functional equivalent" is used herein to describe homologues and fragments of the EV576 protein which retain its ability to bind C5, and to prevent the cleavage of complement C5 by C5 convertase into complement C5a and complement C5b-9. The term "functional equivalent" also refers to molecules that are structurally similar to the EV576 protein or that contain similar or identical tertiary structure, particularly in the environment of the active site or active sites of the EV576 protein that binds to C5, such as synthetic molecules.

The term "homologue" is meant to include reference to paralogues and orthologues of the EV576 sequence that is explicitly identified in FIG. 2, including, for example, the EV576 protein sequence from other tick species, including *Rhipicephalus appendiculatus, R. sanguineus, R. bursa, A. americanum, A. cajennense, A. hebraeum, Boophilus microplus, B. annulatus, B. decoloratus, Dermacentor reticulatus, D. andersoni, D. marginatus, D. variabilis, Haemaphysalis inermis, Ha. leachii, Ha. punctata, Hyalomma anatolicum anatolicum, Hy. dromedarii, Hy. marginatum marginatum, Ixodes ricinus, I. persulcatus, I. scapularis, I. hexagonus, Argas persicus, A. reflexus, Ornithodoros erraticus, O. moubata moubata, O. m. porcinus*, and *O. savignyi*. The term "homologue" is also meant to include the equivalent EV576 protein sequence from mosquito species, including those of the *Culex, Anopheles* and *Aedes* genera, particularly *Culex quinquefasciatus, Aedes aegypti* and *Anopheles gambiae*; flea species, such as *Ctenocephalides felis* (the cat flea); horseflies; sandflies; blackflies; tsetse flies; lice; mites; leeches; and flatworms. The native EV576 protein is thought to exist in *O. moubata* in another three forms of around 18 kDa and the term "homologue" is meant to include these alternative forms of EV576.

Methods for the identification of homologues of the EV576 sequence given in FIG. 2 will be clear to those of skill in the art. For example, homologues may be identified by homology searching of sequence databases, both public and private. Conveniently, publicly available databases may be used, although private or commercially-available databases will be equally useful, particularly if they contain data not represented in the public databases. Primary databases are the sites of primary nucleotide or amino acid sequence data deposit and may be publicly or commercially available. Examples of publicly-available primary databases include the GenBank database, the EMBL database, the DDBJ database, the SWISS-PROT protein database, PIR, TrEMBL, the TIGR databases, the NRL-3D database, the Protein Data Base, the NRDB database, the OWL database and the secondary databases PRO SITE, PRINTS, Profiles, Pfam, Identify and Blocks databases. Examples of commercially-available databases or private databases include PathoGenome (Genome Therapeutics Inc.) and PathoSeq (Incyte Pharmaceuticals Inc.).

Typically, greater than 30% identity between two polypeptides (preferably, over a specified region such as the active site) is considered to be an indication of functional equivalence and thus an indication that two proteins are homologous. Preferably, proteins that are homologues have a degree of sequence identity with the EV576 protein sequence identified in FIG. 2 of greater than 60%. More preferred homologues have degrees of identity of greater than 70%, 80%, 90%, 95%, 98% or 99%, respectively with the EV576 protein sequence given in FIG. 2. Percentage identity, as referred to herein, is as determined using BLAST version 2.1.3 using the default parameters specified by the NCBI (the National Center for Biotechnology Information [Blosum 62 matrix; gap open penalty=11 and gap extension penalty=1].

Homologues of the EV576 protein sequence given in FIG. 2 include mutants containing amino acid substitutions, insertions or deletions from the wild type sequence, for example, of 1, 2, 3, 4, 5, 7, 10 or more amino acids, provided that such mutants retain the ability to bind C5. Mutants thus include proteins containing conservative amino acid substitutions that do not affect the function or activity of the protein in an adverse manner. This term is also intended to include natural biological variants (e.g. allelic variants or geographical variations within the species from which the EV576 proteins are derived). Mutants with improved ability to bind C5 may also be designed through the systematic or directed mutation of specific residues in the protein sequence.

Fragments of the EV576 protein and of homologues of the EV576 protein are also embraced by the term "functional equivalents" providing that such fragments retain the ability to bind C5. Fragments may include, for example, polypeptides derived from the EV576 protein sequence which are less than 150 amino acids, less than 125 amino acids, less than 100 amino acids, less than 75 amino acids, less than 50 amino acids, or even 25 amino acids or less, provided that these fragments retain the ability to bind to complement C5. Included as such fragments are not only fragments of the *O. moubata* EV576 protein that is explicitly identified herein in FIG. 2, but also fragments of homologues of this protein, as described above. Such fragments of homologues will typically possess greater than 60% identity with fragments of the EV576 protein sequence in FIG. 2, although more preferred fragments of homologues will display degrees of identity of greater than 70%, 80%, 90%, 95%, 98% or 99%, respectively with fragments of the EV576 protein sequence in FIG. 2. Fragments with improved may, of course, be rationally designed by the systematic mutation or fragmentation of the wild type sequence followed by appropriate activity assays. Fragments may exhibit similar or greater affinity for C5 as EV576 and may have the same or greater $IC_{50}$ for C5.

A functional equivalent used according to the invention may be a fusion protein, obtained, for example, by cloning a polynucleotide encoding the EV576 protein in frame to the coding sequences for a heterologous protein sequence. The term "heterologous", when used herein, is intended to designate any polypeptide other than the EV576 protein or its functional equivalent. Example of heterologous sequences, that can be comprised in the soluble fusion proteins either at N- or at C-terminus, are the following: extracellular domains of membrane-bound protein, immunoglobulin constant regions (Fc region), multimerization domains, domains of extracellular proteins, signal sequences, export sequences, or sequences allowing purification by affinity chromatography. Many of these heterologous sequences are commercially available in expression plasmids since these sequences are commonly included in the fusion proteins in order to provide additional properties without significantly impairing the specific biological activity of the protein fused to them [14]. Examples of such additional properties are a longer lasting half-life in body fluids, the extracellular localization, or an easier purification procedure as allowed by a tag such as a histidine or HA tag.

The EV576 protein and, functional equivalents thereof, may be prepared in recombinant form by expression in a host cell. Such expression methods are well known to those of skill in the art and are described in detail by [15] and [16]. Recombinant forms of the EV576 protein and functional equivalents thereof are preferably unglycosylated.

The proteins and fragments of the present invention can also be prepared using conventional techniques of protein chemistry. For example, protein fragments may be prepared by chemical synthesis. Methods for the generation of fusion proteins are standard in the art and will be known to the skilled reader. For example, most general molecular biology, microbiology recombinant DNA technology and immunological techniques can be found in [15] or [17].

The subject to which the agent that binds C5 is administered in the method or use of the invention is preferably a mammal, preferably a human. The subject to which the agent that binds C5 is administered may also be suffering from a further disease with which peripheral nerve disorders are associated, such as diabetes mellitus, vasculitis, paraproteinaemia and hereditary motor and sensory neuropathy.

The agent is administered in a therapeutically or prophylactically effective amount. The term "therapeutically effective amount" refers to the amount of agent needed to treat or ameliorate a targeted disease. The term "prophylactically effective amount" used herein refers to the amount of agent needed to prevent a targeted disease.

Preferably, the dose of the agent is sufficient to bind as much available C5 as possible in the subject, more preferably, all available C5. Preferably, the dose of the agent supplied is at least twice the molar dose needed to bind all available C5 in the subject. The dose of the agent supplied may be 2.5 times, 3 times or 4 times the molar dose needed to bind all available C5 in the subject. Preferably, the dose is from 0.0001 mg/kg (mass of drug compared to mass of patient) to 20 mg/kg, preferably 0.001 mg/kg to 10 mg/kg and more preferably 0.1 mg/kg to 1 mg/kg.

The frequency with which the dose needs to be administered will depend on the half-life of the agent involved. Where the agent is the EV576 protein or a functional equivalent thereof, the dose may be administered as a continuous infusion, in bolus doses or on a daily basis, twice daily basis, or every two, three, four days, five, six, seven, 10, 15 or 20 days or more.

The exact dosage and the frequency of doses may also be dependent on the patient's status at the time of administration. Factors that may be taken into consideration when determining dosage include the severity of the disease state in the patient, the general health of the patient, the age, weight, gender, diet, time and frequency of administration, drug combinations, reaction sensitivities and the patient's tolerance or response to therapy.

The precise amount can be determined by routine experimentation, but may ultimately lie with the judgement of the clinician.

The agent will generally be administered as part of a pharmaceutically acceptable carrier. The term "pharmaceutically acceptable carrier", as used herein, includes genes, polypeptides, antibodies, liposomes, polysaccharides, polylactic acids, polyglycolic acids and inactive virus particles or indeed any other agent provided that the carrier does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. The pharmaceutical carrier employed will thus vary depending on the route of administration. Carriers may enable the pharmaceutical compositions to be formulated into tablets, pills, dragees, capsules, liquids, gels, syrups, slurries, suspensions to aid intake by the patient. A thorough discussion of pharmaceutically acceptable carriers is available in [18].

The agent may be delivered by any known route of administration. The agent may be delivered by a parenteral route (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications, needles, and hyposprays.

In one embodiment the agent is administered intravenously at a dose of 13 mg/kg followed by a 12-hourly dose of 4 mg/kg intraperitoneally.

The agent that binds C5 may be administered alone or as part of a treatment regimen also involving the administration of other drugs currently used in the treatment of patients with a peripheral nerve disorder. For example, the agent may be administered in combination with the infusion of immunoglobulin or in combination with plasmapheresis treatment. Combinations of drug treatments may have an additive or synergistic effect on treatment of the disease.

The invention thus provides—(i) an agent that binds C5, preferably the EV576 protein or a functional equivalent thereof, and (ii) immunoglobulin, for use in therapy.

The invention, also provides the use of—(i) an agent that binds C5, preferably the EV576 protein or a functional equivalent thereof, and (ii) immunoglobulin, in the manufacture of a medicament for treating a peripheral nerve disorder.

The agent that binds C5 may be administered simultaneously, sequentially or separately with the other drug(s). For example, the agent that binds C5 may be administered before or after administration of the other drug(s).

The invention thus provides the use of an agent that binds C5, preferably the EV576 protein or a functional equivalent thereof, in the manufacture of a medicament for treating a peripheral nerve disorder in a subject, wherein said subject has been pre-treated with an immunoglobulin. The invention also provides the use of an immunoglobulin in the manufacture of a medicament for treating a peripheral nerve disorder in a subject wherein said subject has been pre-treated with an agent that binds C5, preferably the EV576 protein or a functional equivalent thereof.

The agent that binds C5 may also be administered as part of a treatment regimen also involving the administration of other drugs currently used in the treatment of other diseases with which a peripheral nerve disorder is associated, such as diabetes mellitus, vasculitis, paraproteinaemia and hereditary motor and sensory neuropathy. The agent that binds C5 may be administered simultaneously, sequentially or separately with the other drug(s). For example, the agent that binds C5 may be administered before or after administration of the other drug(s).

Various aspects and embodiments of the present invention will now be described in more detail by way of example. It will be appreciated that modification of detail may be made without departing from the scope of the invention.

BRIEF DESCRIPTION OF FIGURES

FIG. 2: Primary sequence of EV576. Signal sequence underlined. Cysteine residues in bold type. Nucleotide and amino acid number indicated at right. The nucleic acid sequence is designated SEQ ID NO: 1, whereas the amino acid sequence is designated SEQ ID NO: 2.

EXAMPLES

1. Mechanism of Action and Inhibitory Concentration

Figure 1:
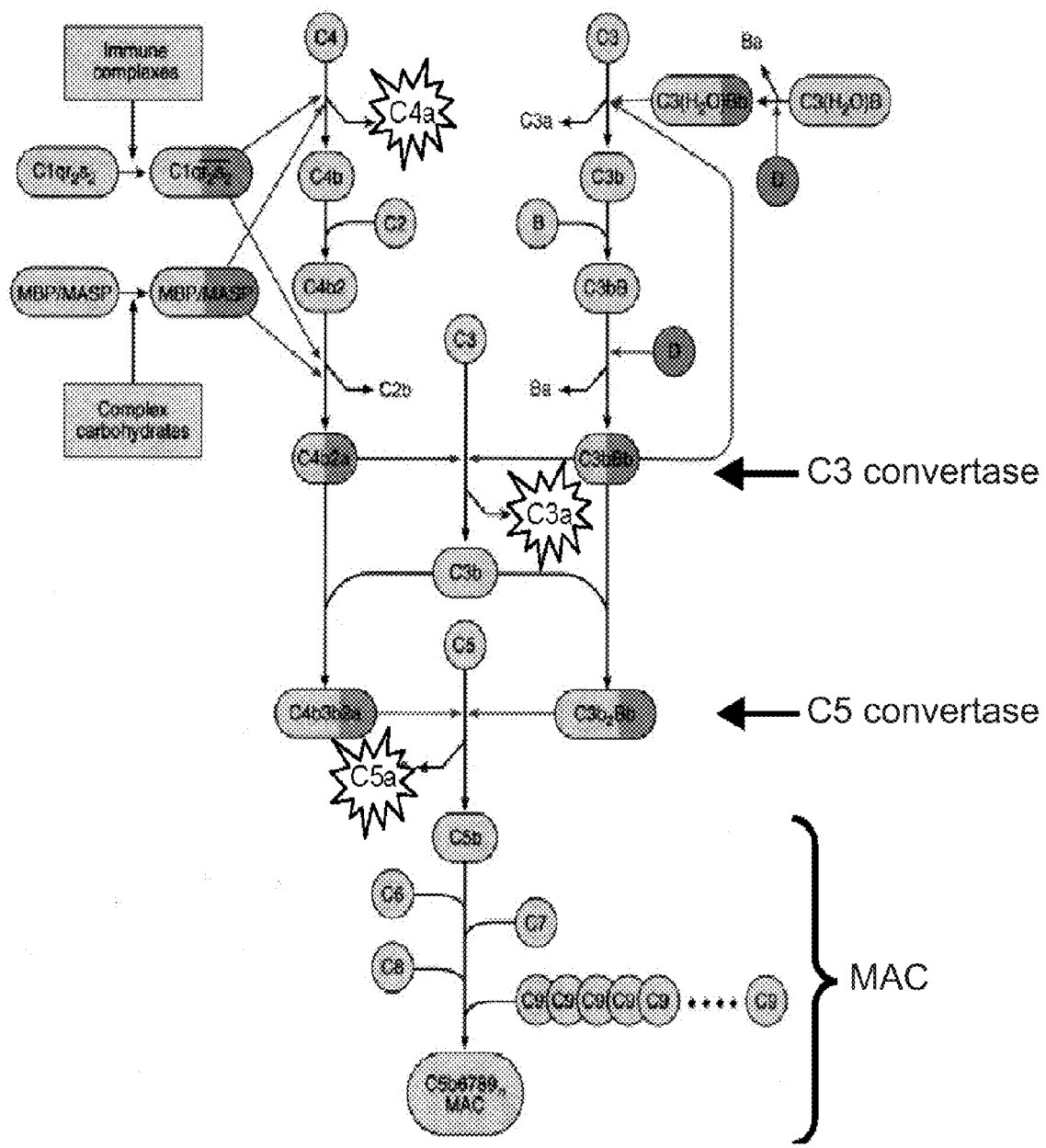
FIG. 1: Schematic diagram of classical and alternative pathways of complement activation. Enzymatic components, dark grey. Anaphylatoxins enclosed in starbursts.
Figure 3A:
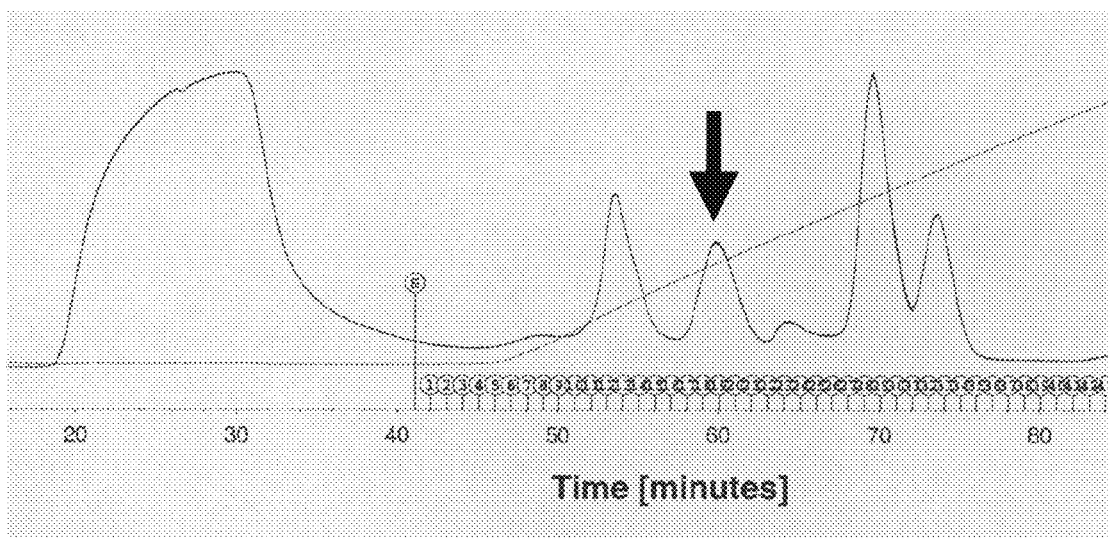
FIG. 3: Purification of EV576 from tick salivary gland extract (SGE). A) Anion exchange chromatography. B) Classical haemolytic assay of fractions. C) Reducing SDS-PAGE. D) RP-HPLC.
Figure 3B:
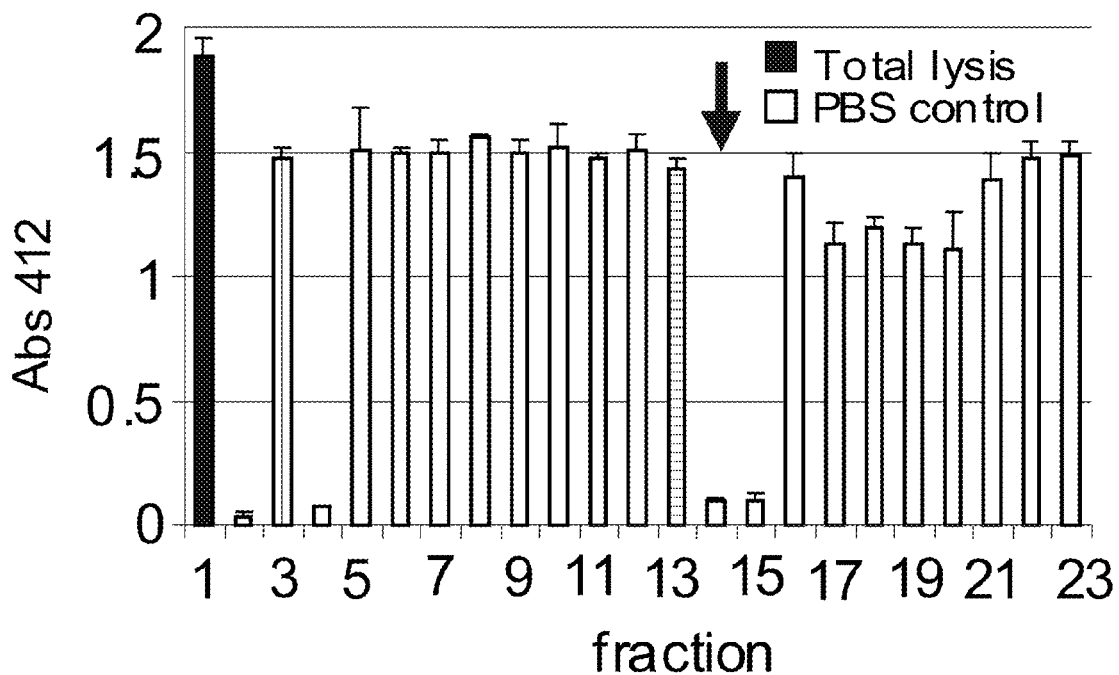

EV576 was purified from salivary gland extracts of the soft tick *Orthinodoros moubata* by SDS-PAGE and RP-HPLC of fractions of salivary gland extract found to contain complement inhibitory activity by classical haemolytic assays (FIG. 3) as disclosed in [19].

Figure 4C:
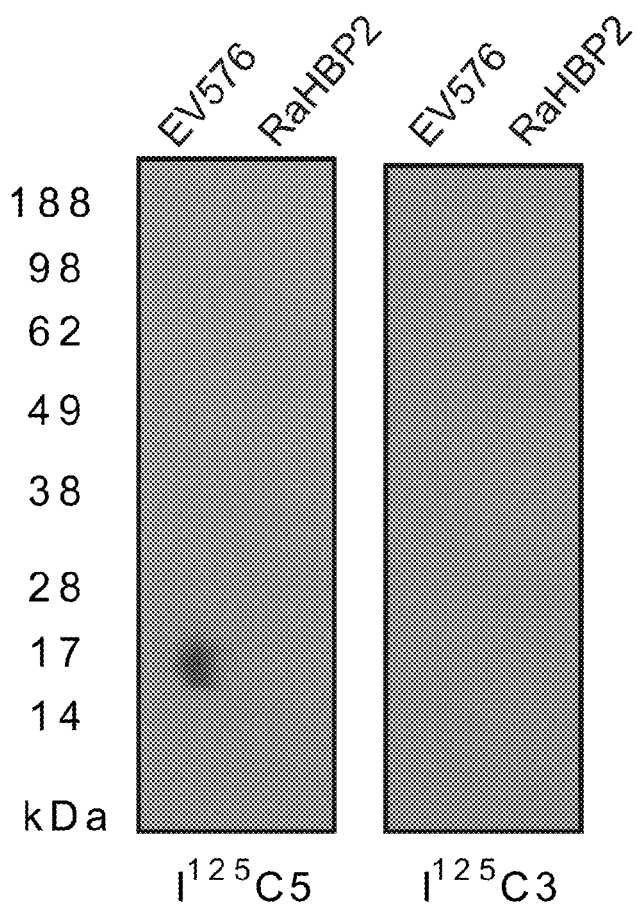
FIG. 4: Mechanism of action of EV576. A) No effect on C3a production. B) Prevents C5a production. C) Binds directly to C5.

EV576 inhibits both human and guinea pig classical and alternative pathways. It has no effect on the rate of C3a production (FIG. 4A) but prevents cleavage of C5a from C5 (FIG. 4B).

The ability of EV576 to inhibit both the classical and the alternative complement pathways is due to binding of the molecule to complement C5, the precursor of C5a and C5b-9. EV576 binds directly to C5 (FIG. 4C) with an $IC_{50}$ of ≈0.02 mg/ml. The precise binding mechanism and accessory roles (if any) played by serum factors are under investigation.

Figure 5B:
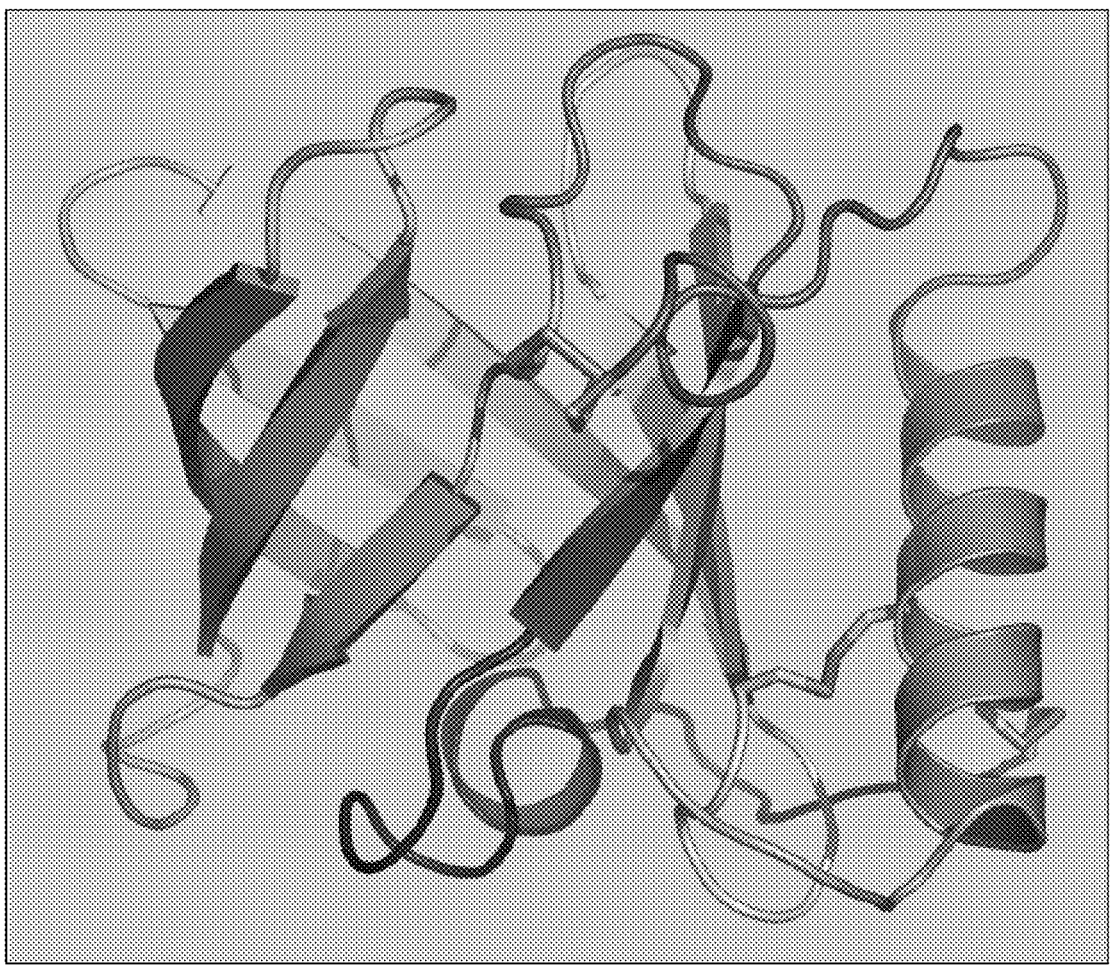
FIG. 5: Recombinant EV576. A) Recombinant EV576 (rEV576) inhibits complement as effectively as native EV576. B) Structure of EV576.

Recombinant EV576 (rEV576) with glycosylation sites removed (which otherwise are glycosylated in the yeast expression system) is as active as the native non-glycosylated protein (FIG. 5A).

The structure of EV576 confirms that it is an outlying member of the lipocalin family (FIG. 5B), having 46% identity with moubatin, a platelet aggregation inhibitor from *O. moubata*. Lipocalins are a large group of soft tick proteins the functions of which, with rare exceptions, are unknown.

2. Effect of EV576 on Experimental Autoimmune Neuritis

Experimental autoimmune neuritis (EAN) was induced in rats according to the method described in reference [20].

Lewis rats were injected with 170 μg peripheral nerve myelin P0 protein peptide 106-124 and 1.5 mg Mycobacterium tuberculosis with Freund's incomplete adjuvant at day 0. At Day 11 after inoculation, 93% of the animals had a score of 2 on the clinical scoring grade. The severity of paresis (paralysis/weakness) was graded as follows: 0=no illness; 1=flaccid tail; 2=moderate paraparesis; 3=severe paraparesis; and 4=tetraparesis or death. At Day 11, the rats were injected with a) 3 mg/rat intravenously followed by 1 mg/rat intraperitoneally at 12-hour intervals for 7 days, b) 0.3 mg/rat intravenously followed by 0.1 mg/rat intraperitoneally at 12-hour intervals for 7 days or c) PBS. Control groups were totally untreated. The treatment was limited to 7 days and then stopped. The animals were then followed until day 38 when the animals were euthanased. The rats were assessed for changes in weight and clinical grade.

All animals lost body weight over the initial 10-day period of treatment. Weight was regained from Day 17-18 until Day 38 when the animal's original body weight was regained (FIG. 6a). There were no significant differences between treatment groups.

Figure 6B:
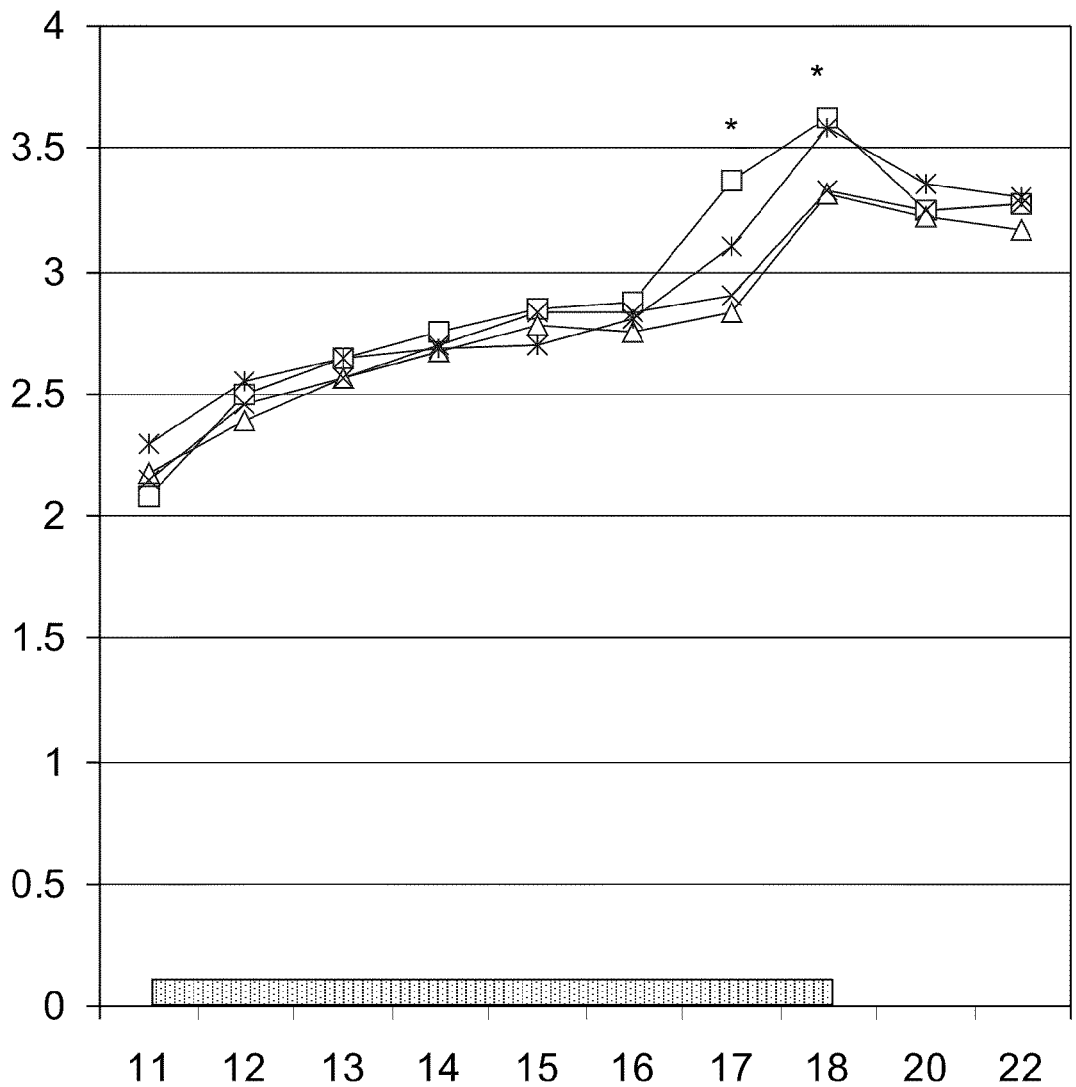
FIG. 6: Effect of rEV576 in experimental autoimmune neuritis model. A) Weight loss in rEV576 treated animals compared with control animals. B) Clinical scores in animals treated with rEV576 compared with control animals.

By Day 11, 93% of animals had a clinical score of 2 with a mean score of 2.17. Treatment occurred from Day 11 to Day 18. On Day 17 and 18, both active treatment groups (i.e. high and low dose rEV576 treated groups), showed statistically significantly lower clinical scores than the untreated group (P<0.001) and the PBS treated group (P<0.01). There was no difference between the two active groups (that is, high and low dose rEV576) (FIG. 6b).

Thus rEV576 given by iv/ip injection reduces the degree of clinical disease even when given during the active disease phase (that is, at a clinical score of 2). Earlier treatment may show greater effect. Thus rEV576 represents a possible human therapy for peripheral nerve disorders such as GBS and CIDP.

[1] Mastellos, D., et al., Clin Immunol, 2005. 115(3): p. 225-35
[2] Kwa., et. al., Brain 2003. 126, 361-375
[3] Stoll, et. al., Ann Neurol 1991. 30:147-155
[4] Guo, R. F. and P. A. Ward, Annu Rev Immunol, 2005.23: p. 821-52
[5] Neumann, E., et al., Arthritis Rheum, 2002. 46(4): p. 934-45
[6] Williams, A. S., et al., Arthritis Rheum, 2004. 50(9): p. 3035-44
[7] Quigg, R. J., Curr Dir Autoimmun, 2004. 7: p. 165-80
[8] Papagianni, A. A., et al., Nephrol Dial Transplant, 2002. 17(1): p. 57-63
[9] He, C., et al., J Immunol, 2005. 174(9): p. 5750-7
[10] Mead, R. J., et al., J Immunol, 2002. 168(1): p. 458-65
[11] Nakashima, S., et al., J Immunol, 2002. 169(8): p. 4620-7
[12] Mizuno, M. and D. S. Cole, Expert Opin Investig Drugs, 2005. 14(7): p. 807-21
[13] Allegretti, M., et al. Curr Med Chem, 2005. 12(2): p. 217-36
[14] Terpe K, Appl Microbiol Biotechnol, 2003. 60: 523-33
[15] Sambrook et al (2000)
[16] Fernandez & Hoeffler (1998)
[17] Ausubel et al. (1991)
[18] Remington's Pharmaceutical Sciences; Mack Pub. Co., N.J. 1991
[19] WO2004/106369
[20] Zhu, J. et al. Acta Neurologica Scandinavica, 1994. 90: p. 19-25

The invention claimed is:

1. A method of treating or preventing a post-infective demyelinating polyradiculoneuropathy (Guillain Barré syndrome) comprising administering to a subject in need thereof a therapeutically or prophylactically effective amount of an agent that binds complement C5, wherein the agent that binds C5 is:

a) a protein comprising or consisting of amino acids 19 to 168 of the amino acid sequence of SEQ ID NO: 2;

b) a protein comprising or consisting of amino acids 1 to 168 of the amino acid sequence of SEQ ID NO: 2;

c) a protein of (a) or (b) having at least 95% sequence identity to amino acids 1 to 168 or amino acids 19-168 of the amino acid sequence of SEQ ID NO: 2, wherein said protein comprises six cysteine residues that are spaced relative to each other at a distance of 32 amino acids apart, 62 amino acids apart, 28 amino acids apart, 1 amino acid apart and 21 amino acids apart as arranged from the amino terminus to the carboxyl terminus of the sequence according to amino acids 1 to 168 of the amino acid sequence of SEQ ID NO: 2, wherein said protein inhibits cleavage of C5 by classical and alternative C5 convertases; or d) a fragment of the complement inhibitor polypeptide of amino acids 19 to 168 of the amino acid sequence of SEQ ID NO: 2, wherein said fragment comprises six cysteine residues that are spaced relative to each other at a distance of 32 amino acids apart, 62 amino acids apart, 28 amino acids apart, 1 amino acid apart and 21 amino acids apart as arranged from the amino terminus to the carboxyl terminus of the sequence according to amino acids 1 to 168 of the amino acid sequence of SEQ ID NO: 2, wherein said fragment inhibits cleavage of C5 by classical and alternative C5 convertases.

2. A method according to claim 1 wherein the agent acts to prevent the cleavage of complement C5 by C5 convertase into complement C5a and complement C5b-9.

3. A method according to claim 1 wherein the agent binds C5 with an $IC_{50}$ of less than 0.2 mg/ml.

4. A method according to claim 1 wherein the agent is derived from a haematophagous arthropod.

5. A method according to claim 1 wherein the subject is a mammal.

6. A method according to claim 1 wherein the agent is administered in a dose sufficient to bind all available C5.

7. A method according to claim 1 wherein the agent is administered intravenously at a dose of 13 mg/kg followed by intraperitoneal injections of 4 mg/kg every 12 hours.

8. A method according to claim 1 wherein the agent that binds C5 is administered as part of a treatment regimen also involving the administration of a further drug for the treatment of a post-infective demyelinating polyradiculoneuropathy (Guillain Barré syndrome).

9. A method according to claim 8 wherein the further drug is immunoglobulin.

10. A method according to claim 8 wherein the agent that binds C5 is administered simultaneously, sequentially or separately with the further drug.

11. A method according to claim 1 wherein the post-infective demyelinating polyradiculoneuropathy (Guillain Barré syndrome) is selected from the group consisting of Miller Fisher syndrome, acute inflammatory demyelinating polyradiculoneuropathy (AIDP), and chronic inflammatory demyelinating polyradiculoneuropathy (CIDP).

12. The method according to claim 1 wherein the protein of (c) having at least 95% sequence identity to amino acids 1 to 168 or amino acids 19-168 of the amino acid sequence of SEQ ID NO: 2 has at least 98% sequence identity to amino acids 1 to 168 or amino acids 19-168 of the amino acid sequence of SEQ ID NO: 2.

13. A method according to claim 1 wherein the subject is a human.

* * * * *

SEQUENCE LISTING

<160> NUMBER OF SEQ ID NOS: 2

<210> SEQ ID NO 1
<211> LENGTH: 507
<212> TYPE: DNA
<213> ORGANISM: Ornithodoros moubata

<400> SEQUENCE: 1

```
atgctggttt tggtgaccct gattttctcc ttttctgcga acatcgcata tgctgacagc      60
gaaagcgact gcactggaag cgaacctgtt gacgccttcc aagctttcag tgagggcaaa     120
gaggcatatg tcctggtgag gtccacggat cccaaagcga gggactgctt gaaaggagaa     180
ccagccggag aaaagcagga caacacgttg ccggtgatga tgacgtttaa gaatggcaca     240
gactgggctt caaccgattg gacgtttact ttggacggcg caaaggtaac ggcaaccctt     300
ggtaacctaa cccaaaatag gaagtggtc tacgactcgc aaagtcatca ctgccacgtt     360
gacaaggtcg agaaggaagt tccagattat gagatgtgga tgctcgatgc gggagggctt     420
gaagtggaag tcgagtgctg ccgtcaaaag cttgaagagt tggcgtctgg caggaaccaa     480
atgtatcccc atctcaagga ctgctag                                         507
```

<210> SEQ ID NO 2
<211> LENGTH: 168
<212> TYPE: PRT
<213> ORGANISM: Ornithodoros moubata

<400> SEQUENCE: 2

```
Met Leu Val Leu Val Thr Leu Ile Phe Ser Phe Ser Ala Asn Ile Ala
1               5                   10                  15

Tyr Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
145                 150                 155                 160

Met Tyr Pro His Leu Lys Asp Cys
                165
```